United States Patent [19]

Seifter et al.

[11] Patent Number: 5,476,516
[45] Date of Patent: Dec. 19, 1995

[54] ANTICALCIFICATION TREATMENT FOR ALDEHYDE-TANNED BIOLOGICAL TISSUE

[75] Inventors: Eli Seifter, New Hyde Park; Robert W. M. Frater, Bronxville, both of N.Y.

[73] Assignee: Albert Einstein College of Medicine of Yeshiva University, Bronx, N.Y.

[21] Appl. No.: 849,940

[22] Filed: Mar. 13, 1992

[51] Int. Cl.$^6$ .............................. C14C 3/16; C14C 3/28; A61F 2/24; A61F 2/02
[52] U.S. Cl. .................. 8/94.11; 8/94.21; 623/1; 623/2; 623/11; 623/12; 623/66; 623/901; 128/DIG. 8
[58] Field of Search .................. 8/94.11, 94.21; 623/1, 2, 3, 11, 12, 13, 66, 901; 128/DIG. 8; 424/423, 424

[56] References Cited

U.S. PATENT DOCUMENTS

| | | | |
|---|---|---|---|
| 4,323,358 | 4/1982 | Lentz et al. | 8/94.11 |
| 4,378,224 | 3/1983 | Nimni et al. | 8/94.11 |
| 4,402,697 | 9/1983 | Pollock et al. | 8/94.11 |
| 4,405,327 | 9/1983 | Pollock | 8/94.11 |
| 4,481,009 | 11/1984 | Nashef | 8/94.11 |
| 4,553,974 | 11/1985 | Dewanjee | 8/94.11 |
| 4,647,283 | 3/1987 | Carpentier et al. | 8/94.11 X |
| 4,648,881 | 3/1987 | Carpentier et al. | 8/94.11 X |
| 4,770,665 | 9/1988 | Nashef | 8/94.11 |
| 4,786,287 | 11/1988 | Nashef et al. | 8/94.21 |
| 4,838,888 | 6/1989 | Nashef | 8/94.11 X |
| 4,885,005 | 12/1989 | Nashef et al. | 8/94.11 |
| 4,911,713 | 3/1990 | Sauvage et al. | 8/94.11 X |
| 4,976,733 | 12/1990 | Girardot | 8/94.11 X |
| 5,002,566 | 3/1991 | Carpentier et al. | 8/94.28 X |
| 5,215,541 | 6/1993 | Nashef et al. | 8/94.11 |

FOREIGN PATENT DOCUMENTS 2180755   4/1987   United Kingdom .

*Primary Examiner*—Douglas J. McGinty
*Attorney, Agent, or Firm*—Amster, Rothstein & Ebenstein

[57] ABSTRACT

A method of treating aldehyde-tanned biological tissue minimizes in vivo calcification and reduces cytotoxicity without impairing the mechanical strength of the tanned tissue. The method includes the step of treating the aldehyde-tanned biological tissue with at least one liquid polyol having the formula:

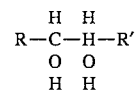

where R is $CH_2OH$ or an alkyl group, and R' is H, an alkyl group or an O-acyl where the acyl is $C_2$–$C_9$ or a carboxyalkyl; or

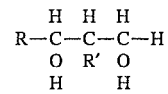

where R is H or an alkyl group, and R' is H, an alkyl group, O-alkyl or O-carboxyalkyl. Preferred polyols are propylene glycol, 1,3-propanediol, 2,3-butylene glycol and glycerol, and the polyol is preferably a diol.

7 Claims, No Drawings

ANTICALCIFICATION TREATMENT FOR ALDEHYDE-TANNED BIOLOGICAL TISSUE

BACKGROUND OF THE INVENTION

The present invention relates to an anticalcification treatment for aldehyde tanned biological-tissue, and more particularly to such a treatment which minimizes in vivo calcification and reduces cytotoxicity without impairing the mechanical strength of the tanned tissue.

When biological tissue containing the amino groups ($NH_2$) characteristic of protein are treated with glutaraldehyde ($CHO(CH_2)_3CHO$), the glutaraldehyde links the amino-containing proteins together in cross-linking reactions. One of the resulting cross-linked products is devoid of any free aldehyde groups because both aldehyde groups of the glutaraldehyde react with different amino groups, but the other resulting cross-linked product retains a free aldehyde group because both amino groups react with the same aldehyde group of the glutaraldehyde. As both types of cross-linked products are present in equilibrium with each other, the glutaraldehyde-tanned biological tissue will always contain free aldehyde groups.

The free aldehyde groups in an implant are associated with the induction of a local inflammatory reaction and subsequent calcification of the graft. While vigorous washing of the aldehyde-treated tissue is effective to remove unreacted glutaraldehyde, it is ineffective to remove the free aldehyde groups of the glutaraldehyde which has reacted with the tissue protein. The known treatments (e.g., amino acids in an acidic buffer) of the aldehyde-tanned biological tissue to remove the free aldehyde groups from the glutaraldehyde which has reacted with the tissue protein result in an impairment of the mechanical strength of the tanned tissue, thereby frustrating the very purpose of the tanning treatment.

Bioprosthetic heart valves in current use around the world are made or porcine aortic valves or bovine pericardium tanned with glutaraldehyde. Biological arterial substitutes are made of xenograft or homograft vessels treated with glutaraldehyde treated bovine pericardium. Artificial heart valves made from glutaraldehyde treated tissue are excellent substitutes for diseased natural valves, with a particularly low risk of thromboembolism. Their utility is, however, compromised by the aforementioned tendency to calcification which occurs in almost 100% of children within 5 years after implantation. Adults with hyperparathyroidism or renal failure share this tendency. Calcification causes failure of the implants, and the need for re-replacement is a bar to frequent use thereof except in the elderly.

The alternative of bioprosthetic valve replacement using untanned tissue is unacceptable since the untanned tissue undergoes partial digestion and resorption, loses its strength over time and eventually ruptures. Tanning of the tissue with aldehyde minimizes or prevents its loss of strength over time.

The alternative of mechanical valve replacement carries with it the significant disadvantages of an absolute requirement for anticoagulation (to prevent valve thrombosis) and a continuing incidence of emboli, even with proper anticoagulation. These problems are magnified in the Third World, where large numbers of children have valvular heart disease and difficulty with anticoagulation management is accompanied by an excessive rate of both thrombosis and hemorrhage.

A bioprosthetic valve that did not calcify would become the valve of choice, replacing not only all bioprosthetic valves in current use, but being preferred also in a substantial number of those cases where mechanical valves are in current use. Such a valve would make possible an increase in valve replacement surgery and would improve results, especially in developing countries. Tanned biological tissue for other uses has a smaller commercial production, but the behavior and possibilities for improved preparation are similar. To date, however, no successful anticalcification treatment has been described.

Artificial heart valves made from aldehyde tanned tissue have the further disadvantage of a cytotoxicity which inhibits endothelialization of implants made therefrom. While the cytotoxicity presents less of a problem to the use of aldehyde tanned implants than the calcification potential thereof, it remains a problem which impedes the widespread adoption of aldehyde tanned implants, especially where endothelialization of the implant is deemed critical.

Accordingly, it is an object of the present invention to provide a method of treating aldehyde tanned biological tissue to minimize in vivo calcification.

Another object is to provide such a treatment method without diminution of the mechanical strength gained by tanning with aldehydes.

A further object is to provide such a treatment method which also reduces the cytotoxicity of aldehyde tanned implants that would otherwise inhibit endothelialization of implants.

It is also an object of the present invention to provide such a treatment method which is simple, economical and safe.

SUMMARY OF THE INVENTION

The above and related objects of the present invention are obtained in a method of treating aldehyde-tanned biological tissue to minimize in vivo calcification. The method comprises the step of treating the aldehyde-tanned biological tissue with at least one liquid polyol having the formula:

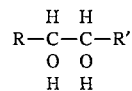

where R is $CH_2OH$ or an alkyl group, and R' is H, an alkyl group or an O-acyl where the acyl is $C_2$–$C_9$ or carboxyalkyl;

or

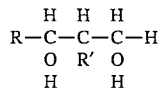

where R is H or an alkyl group, and R' is H, an alkyl group, O-alkyl or O-carboxyalkyl.

In a preferred embodiment the polyol is selected from the group consisting of propylene glycol (actually 1,2-propanediol), propanediol (actually 1,3-propanediol), 2,3-butylene glycol and glycerol. The polyol is preferably a diol, and in particular propylene glycol. Preferably the polyol is a liquid at room temperature, substantially solvent-free, and forms a ring adduct of the aldehyde, especially a ring adduct that has 5 or 6 members.

The alkyl group is preferably $C_1$–$C_5$.

A preferred method involves treating aldehyde-tanned biological tissue with at least one substantially solvent-free liquid diol selected from the group consisting of propylene glycol, propanediol and 2,3-butylene glycol that forms a 5–6 member ring adduct of the aldehyde.

The treatment reduces cytotoxicity of the tanned tissue without impairing the mechanical strength of the tanned tissue.

DETAILED DESCRIPTION OF THE PREFERRED EMBODIMENTS

According to the present invention, aldehyde tanned biological tissue is treated to minimize in vivo calcification and furthermore to reduce cytotoxicity of the tanned tissue without impairing the mechanical strength of the tanned tissue. Depending upon the intended use of the tanned tissue, the untreated biological tissue may be tanned using any of a number of a conventional aldehyde tanning agents, glutaraldehyde being preferred because it contains a pair of aldehyde groups instead of just one and thus enhances the likelihood of cross-linking the biological tissue proteins because there are two reaction mechanisms possible.

The method of the present invention resides in the step of treating the aldehyde-tanned biological tissue with at least one liquid polyol having the formula:

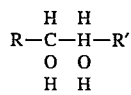

where R is $CH_2OH$ or an alkyl group, and

R' is H, alkyl group or an O-acyl where the acyl is $C_2$–$C_9$ or a carboxyalkyl;

or

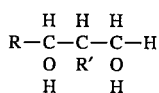

where R is H or an alkyl group, and

R' is H, an alkyl group, O-alkyl or O-carboxyalkyl.

The polyols useful in the present invention are preferably liquid at room temperature and substantially solvent-free (that is, they are used in their concentrated form). The polyols that are liquid at room temperature are preferred for both their chemical reactivity and ease of sterilization. Furthermore, diols that are solid at room temperature tend to dry out the tissue and render it less supple. The polyols that are solvent-free (at least 99% pure) are preferred because the presence of solvents introduces additional functional groups which may undergo reaction with the amino groups of the tissue protein and thus impede the development of cross-linking in the aldehyde tanned tissue since the aldehyde tanning mechanisms are reversible. However polyol solutions which are at least 60% polyol are also useful.

The preferred polyols for use in the present invention are the diols propylene glycol ($H(CHOH)_2CH_3$) (also known as 1,2-propanediol), 1,3-propanediol ($(CH_2OH)_2CH_2$), and 2,3-butylene glycol ($CH_3(CHOH)_2CH_3$) and the triol glycerol ($(CH_2OH)_2CHOH$). Other diols, such as the butanediols and pentanediols, have also been shown to be effective in the process of the present invention. Indeed, the use of larger alkyl groups ($C_4$, $C_5$, etc.) for the R and R' substituents increases lipid solubility without diminishing the chemical bonding of the free aldehydes and increases the plasticity of the treated tissue without weakening the cross-linking thereof. Apparently the chain length between the hydroxyl groups is more significant than the overall chain length or the chain length of any substituents.

The disubstituted diols, such as the various propanediols and 2,3-butylene glycol, display enhanced stability and greater effectiveness in the present invention than the trisubstituted triols, such as glycerol. Transition states containing free hydroxyl groups are susceptible to hydrolysis and yield the undesirable free aldehyde, while transition states based on bonding of free hydroxyl groups are not formed from diol adducts. Thus, the diols are more effective aldehyde blocking agents than the polyols and have been shown to diminish aldehyde-induced calcification. The preferred diol is propylene glycol.

While a variety of different diols may be used in the method of the present invention, it has been discovered that those diols which yield 5- or 6-membered ring adducts of the aldehydes are better inhibitors of calcification than the triols or other polyols since the ring adducts are more stable. More particularly, the preferred diols of the present invention give rise to 1,3-dioxolane rings or 1,3-dioxane rings. Glycerol can also form both dioxolane and dioxane rings with glutaraldehyde treated tissue, the two ring forms existing in equilibrium with one another. However, both of the ring adducts formed from glycerol include free hydroxyl groups attached to the ring (either directly or indirectly), while the diols adducts do not contain free hydroxyl groups and are thus more stable.

According to in vitro testing, glutaraldehyde tanned tissue treated according to the present invention, when inoculated with vascular endothelial cells, developed an endothelial layer, whereas untreated glutaraldehyde tanned tissue did not. Thus the present invention provides a means for increasing the likelihood of an implant formed therefrom fitting into its attachment smoothly and thereafter functioning appropriately.

According to in vivo testing, the implants of glutaraldehyde tanned tissue treated according to the present invention retained their physical integrity (i.e., tensile strength) and were more supple and less rigid compared with untreated glutaraldehyde tanned tissue. The enhanced physical integrity, suppleness and lower rigidity further enhance the utility of the tissue as a prosthetic valve replacement.

While treatment according to the present invention of fresh biological tissue (that is, biological tissue which has not been aldehyde tanned) decreases the mechanical strength of the tissue, the treatment according to the present invention after aldehyde tanning enhances the valve strength while preventing calcification.

More particularly, according to the method of the present invention, the aldehyde tanned tissue is washed with saline to remove excess unreacted aldehyde. The washed tissue is then treated with a polyol according to the present invention and stored, ready for use. If desired, the polyol treatment may be combined (i.e., performed simultaneously) with the saline washes.

The materials treated according to the present invention may be used as heart valves, vessels, esophageae, tracheae, tendons, ligaments, fasciae, membranes and parts of these structures.

EXAMPLE I

This example compares the calcium contents after 70 days of implantation of (a) fresh tissue (that is, tissue which has been neither tanned nor treated according to the present invention), (b) glutaraldehyde tanned tissue not treated according to the present invention, (c) and glutaraldehyde tanned tissue treated according to the present invention (either with glycerol or propylene glycol).

Fresh bovine pericardium was tanned with 0.6% glutaraldehyde (Glu), washed with saline, and transferred to vessels containing either a diol (i.e., propylene glycol) or a triol (i.e., 60% or 99% by wt. glycerol). The material was then implanted in rats, as were specimens of fresh tissue and untreated tanned tissue.

After 70 days, the implants were retrieved and the calcium contents thereof determined in micrograms of calcium per milligram of biological tissue, on a dry weight basis. The results are reported in TABLE 1, along with the Standard Deviations (S.D.) and the number of rats tested in each case.

TABLE 1

| | Fresh | Glu | Glu + 99% glycerol | Glu + 60% glycerol | Glu + propylene glycol |
|---|---|---|---|---|---|
| CALCIUM CONTENT (MICROGRAMS/MG DRY WEIGHT) | | | | | |
| Calcium content | 0.38 | 232.29 | 8.50 | 188.36 | 1.0 |
| S.D. +/− | 0.11 | 13.01 | 0.44 | 11.04 | 0.77 |
| Number of rats | 10 | 10 | 8 | 10 | 10 |

Whereas the glutaraldehyde (GLU) tanning enhanced tissue calcification relative to fresh tissue, substantially pure (99%) glycerol treatment of tanned tissue according to the present invention moderated the calcification and propylene glycol (PG) treatment of tanned tissue according to the present invention was even more effective in inhibiting calcification.

EXAMPLE II

TABLE 2

In TABLE 2 data are presented from an experiment run in parallel with that used to obtain data presented in TABLE 1. The purpose of the experiment was to determine the effects of the treatments described in this application on properties related to the mechanical strength of retrieved implants. Maximum tensile stress ($S_{max}$) and hydroxyproline content (OHP) were determined for (a) glutaraldehyde fixed (Glu.), (b) glutaraldehyde fixed and propylene glycol treated (Glu.+ PG) and (c) unfixed glycerol treated bovine pericardium strips.

TABLE 2

| | Glu. | Glu. + PG | 99% Glycerol |
|---|---|---|---|
| Not implanted | | | |
| No. of Rats | 7 | 7 | 7 |
| $S_{max}$ (kg/mm$^2$) | 0.82 ± 0.28 | 0.86 ± 0.24 | 0.83 ± 0.30 |
| OHP (ug/mg) | 15.2 ± 2.6 | 14.8 ± 2.1 | 13.4 ± 2.90 |
| 70 days after implantation | | | |
| No. of Rats | 7 | 7 | 7 |
| $S_{max}$ (kg/mm$_2$) | 1.02 ± 0.35 | 0.96 ± 0.39 | 0.14 ± 0.16* |
| OHP (ug/mg) | 9.11 ± 1.1 | 9.65 ± 2.4 | 7.84 ± 2.40 |

Glu. vs. Glu. ± PG p > .05; *Glycerol vs. Glu. or Glu. ± PG, p < .001.

TABLE 2-continued

| | P Values | | |
|---|---|---|---|
| | Not Implanted (0 time) | (70 days) | Implanted |
| | Glu | Glu + PG | Glycerol |
| Smax | >.05 | >.1 | <<.001 |
| OHP | <.01 | <.05 | <.05 |

| Tensile stresses of implanted tissues | |
|---|---|
| Glu vs. Glu + PG | p > .05 |
| Gly vs. Glu | p < .001 |
| Gly vs. Glu + PG | p < .001 |

Note:
Without glutaraldehyde, implant loses about 5/6 of its tensile stress (strength). Thus, Glu + PG provides increased strength without calcific changes due to Glu.

EXAMPLE III

The following is a description of a specific experiment and the results obtained in that experiment. In parentheses are comments of ranges of variables from other experiments not detailed herein.

Tissue

1. Bovine Pericardium:

Fresh bovine pericardium was delivered on ice from Max Insel Cohen Inc. immediately after calves were sacrificed. The pericardium was washed under cold tap water for 30 minutes as its fat and vessels were trimmed away, and the pericardium was cut into 1 cm$^2$ pieces. Then the pericardium was rinsed in normal saline for 10 minutes before further treatments.

2. Porcine Aortic Valves:

Fresh porcine aortic valves were delivered on ice from Max Insel Cohen Inc. immediately after pigs were sacrificed. The cusps were cut from the surrounding tissues and washed under cold tap water for 10 minutes and then cut into 1 cm$^2$ pieces. Then the cusps were rinsed in normal saline for 10 minutes before further treatments.

Material Preparation

Glutaraldehyde (25%) was obtained from Fisher Scientific Company and was diluted to 0.625% glutaraldehyde solution with unbuffered normal saline pH=6.2. (In other experiments, isotonic solutions of phosphate buffers (pH 6.8–7.4) were used as diluents; tonicity (strength of the fixation solution) during the fixation process is important to preserve structure. As described in "Treatments" below, all tissues were washed free of free glutaraldehyde and buffers before post-fixation treatment, storage-preservation or implantation, by numerous rinses with saline or water. This is necessary because both the presence of aldehyde and the phosphate buffer favor calcification.

In the study reported here, fixation occurred by placing tissue in fixative for 48 hours, the minimum time required for maximum cross-linking. The degree of cross-linking is determined mainly by pH, strength of the aldehyde solution and volume of the solution used. In the present study, 18 squares of tissue (1 cm$^2$ each) were placed in flasks containing 100 ml of fixative.

Propylene glycol (100%) was obtained from Fisher Scientific Company and was filtered through 0.22 micron nylon member filter before use. (In other experiments propylene glycol was used as a 60% solution prepared with distilled water as diluent. Whereas tonicity of the fixative (aldehyde) and the post-fixation treatment (glycol) is rather important, tonicity of the preserving solution is less so. Preferred solutions of the glycol are between 60–100% active ingredient.) In the present study, specimens were stored in 100% propylene glycol.

Treatments

Control group: Pericardium was preserved in 0.625% glutaraldehyde at 20° C. for 10–14 days.

Propylene glycol group: Pericardium was fixed in 0.625% glutaraldehyde at 20° C. for 2 days, then fully washed in normal saline (10 minutes ×3 times), and finally put into 100% propylene glycol solution at 20° C. for 7–10 days.

Before implantation, both groups of pericardial pieces were washed with normal saline for 10 minutes ×3 times.

Porcine aortic valve cusp strips and bovine pericardial strips were treated identically. (It is to be noted that control pericardia and porcine aortic valve strips were fixed for 10–14 days, whereas experimental strips were fixed for 2–8 days and preserved for 7–10 days. This was done so that only strips from a single batch of pericardia or aortic valves would be used in a given experiment. It was believed justified because earlier experiments with glutaraldehyde fixations showed no change in breaking strength of tissue fixed for time periods of 2 days or more (e.g., 18 days) and changing fixation times did not influence breaking strength, collagen content or calcium content of implanted tissues.)

Experimental Design I

Groups of nine 70–100 g male Sprague Dawley rats were used. To study the effect of fixation and preservation on the strength of the implanted tissue, two groups of nine rats each were studied. One group was designated to be sacrificed at 45 days, the other at 90 days. Under pentobarbital anesthesia, rats received a 3 cm paravertebral full thickness dermal incision and 2 subcutaneous pouches were fashioned. In one pouch, a 3 cm strip of washed glutaraldehyde-fixed pericardial tissue was implanted. The other pouch received a similar strip that had been glutaraldehyde-fixed and then placed in propylene glycol for 8 days. One group of animals was sacrificed at 45 days, and the other at 90 days.

The retrieved implants were studied in a tensiometer to determine stress (i.e., the force required to break the tissue divided by the area $kg/m^2$), a measure of the strength of the tissue. The retrieved implants were also studied for strain (i.e., the change in length (dL) at the break point divided by the initial length ($L_o$)), a measure of elasticity of the tissue.

Results

The results are reported in TABLE 3 and indicate that propylene glycol treatment does not significantly alter either the strength or elasticity of glutaraldehyde-fixed pericardial strips. The results also show that, in the short period of the study, the strips did not lose mechanical strength with time.

TABLE 3

| Bovine Pericarbdium | Glu + PG | Glu |
|---|---|---|
| Post 45 days implantation | | |
| Stress | 1.02 ± .36 | 1.01 ± .38 |
| Strain | .73 ± .25 | .63 ± .13 |
| Post 90 days implantation | | |
| Stress | 1.0 ± .24 | .87 ± .36 |

TABLE 3-continued

| Bovine Pericarbdium | Glu + PG | Glu |
|---|---|---|
| Strain | .58 ± .25 | .58 ± .17 |

Experimental Design II

Four groups of nine rats each were used to study the effects of propylene glycol treatment of glutaraldehyde-fixed bovine pericardial pieces and porcine aortic valve tissue on the collagen and calcium contents of such implants.

Four groups of nine rats each were established. As described earlier, under pentobarbital anesthesia, all rats were subjected to a 2 cm dorsal skin incision and two subcutaneous pouches were established in each rat and implanted in each case with a glutaraldehyde-fixed 1 $cm^2$ tissue in one pouch and a glutaraldehyde-fixed, propylene glycol-preserved 1 $cm^2$ tissue in the other pouch. Two of the groups received implants of bovine pericardial strips, one glutaraldehyde-fixed and the other glutaraldehyde-fixed and propylene glycol-treated. Animals of one group were sacrificed after 45 days, their implants retrieved and analyzed for calcium and hydroxyproline; the other group was studied after 90 days. In parallel, two groups received (in place of bovine pericardium) implants of porcine aortic valve tissue fixed in glutaraldehyde and glutaraldehyde-fixed, propylene glycol-treated tissue. The design for the porcine aortic valve study was the same as for the bovine pericardial tissue study.

Results

The results are reported in TABLE 4 and show treatment with propylene glycol diminishes the rate of calcification due to glutaraldehyde fixation. This is true for both pericardial and aortic valve tissue implants. Collagen is preserved by propylene glycol and, in fact, may actually increase in the case of aortic valve tissue. Thus, propylene glycol inhibits calcification of implants without being harmful to tissue strength.

TABLE 4

| Bovine Pericardium | Glut + PG | Glut |
|---|---|---|
| Post 45 days implantation | | |
| Calcium | 3.0 ± 2.88 | 79.9 ± 41.54* |
| Hydroxyproline | 8.37 ± 1.13 | 8.01 ± 0.47 |
| Post 90 days implantation | | |
| Calcium | 10.45 ± 5.72 | 214.43 ± 34.34 |
| Hydroxyproline | 9.41 ± 1.00 | 8.10 ± 0.74# |
| Porcine Aortic Value | Glut + PG | Glut |
| Post 45 days implantation | | |
| Calcium | 3.68 ± 5.85 | 141.48 ± 58.17* |
| Hydroxyproline | 5.42 ± 1.84 | 3.58 ± 1.48# |
| Post 90 days implantation | | |
| Calcium | 2.78 ± 4.5 | 199.33 ± 53.44* |
| Hydroxyproline | 6.20 ± 0.56 | 4.25 ± 0.65# |

*paired t test (9 in each set) < .001
paired t test (9 in each set) < .005

To summarize, the present invention provides a method of treating aldehyde tanned biological tissue to minimize in vivo calcification without diminution of the mechanical strength gained by tanning with aldehydes and while also reducing the toxicity of aldehyde tanned implants that would otherwise inhibit endothelialization of implants. The treatment method is simple, economical and safe.

Now that the preferred embodiments of the present invention have been described in detail, various modifications and improvements thereon will become readily apparent to those skilled in the art. Accordingly, the spirit and scope of the present invention is to be construed broadly and limited only by the appended claims, and not by the foregoing specification.

We claim:

1. A method of treating glutaraldehyde-tanned biological tissue for use in bioprosthetic valves and the like to minimize in vivo calcification and reduce cytotoxicity of the tanned tissue without impairing the mechanical strength of the tanned tissue, comprising the step of:

treating the glutaraldehyde-tanned biological tissue with at least substantially solvent-free 1,2-propanediol to form a 5 member ring adduct of the glutaraldehyde.

2. The method of claim 1 wherein the 1,2-propanediol is a liquid at room temperature.

3. The method of claim 1 wherein said treating reduces cytotoxicity of the tanned tissue without impairing the mechanical strength of the tanned tissue.

4. The method of claim 1 wherein the biological tissue is bovine pericardium.

5. The method of claim 1 wherein the biological tissue is porcine aortic valve.

6. The method of claim 1 wherein the step comprises treating the glutaraldehyde-tanned biological tissue with a composition consisting essentially of said 1,2-propanediol.

7. The method of claim 1 wherein the step comprises treating the glutaraldehyde-tanned biological tissue with a composition consisting essentially of said 1,2-propanediol which is at least 60% by weight pure.

* * * * *